(12) United States Patent
Schmenger et al.

(10) Patent No.: US 7,320,711 B2
(45) Date of Patent: Jan. 22, 2008

(54) DYESTUFF FOR KERATIN FIBERS

(75) Inventors: Juergen Schmenger, Weiterstadt (DE); Petra Braun, Muenster (DE)

(73) Assignee: Wella AG, Darmstadt (DE)

( * ) Notice: Subject to any disclaimer, the term of this patent is extended or adjusted under 35 U.S.C. 154(b) by 289 days.

(21) Appl. No.: 10/537,073

(22) PCT Filed: May 3, 2004

(86) PCT No.: PCT/EP2004/004631

§ 371 (c)(1),
(2), (4) Date: Jun. 1, 2005

(87) PCT Pub. No.: WO2005/044207

PCT Pub. Date: May 19, 2005

(65) Prior Publication Data

US 2006/0121070 A1    Jun. 8, 2006

(30) Foreign Application Priority Data

Oct. 10, 2003   (DE) ................................. 103 47 243

(51) Int. Cl.
*A61K 7/13* (2006.01)

(52) U.S. Cl. .................. 8/405; 8/406; 8/407; 8/431; 8/463; 8/619; 510/349; 510/441

(58) Field of Classification Search ............. 8/405, 8/406, 407, 431, 463, 619; 510/349, 441
See application file for complete search history.

(56) References Cited

U.S. PATENT DOCUMENTS 4,407,231 A    10/1983   Colborn et al.
5,382,433 A    1/1995    Pahlck et al.
5,733,272 A *  3/1998    Brunner et al. ............. 604/359

FOREIGN PATENT DOCUMENTS

| DE | 100 08 305 A1 | 9/2001 |
| EP | 1 346 720 | 9/2003 |
| WO | 95/16432 | 6/1995 |
| WO | 00/36931 | 6/2000 |
| WO | 01/05358 A1 | 1/2001 |
| WO | 01/43784 A2 | 6/2001 |

OTHER PUBLICATIONS

Sagarin, E.: "Cosmetics, Science and Technology", Interscience Publishers Inc., New York, 1957, pp. 503-507.

H. Janistyn: "Hand Buch Der Kosmetika Und Riechstoffe", Band 3, 1973, pp. 388-397.

K. Schrader: "Grundlagen Und Rezepturen Der Kosmetika" 2. Auflage 1989, pp. 872-815.

* cited by examiner

*Primary Examiner*—Eisa Elhilo
(74) *Attorney, Agent, or Firm*—Michael J. Striker

(57) ABSTRACT

The colorant for keratin fibers contains direct and/or oxidative dyes as well as a perfume system consisting of an encapsulated perfume and an unencapsulated perfume of the same composition. The ratio of encapsulated perfume to unencapsulated perfume is equal to about 0.5:3 to 3:0.5. The perfume system is used for removing or masking the unpleasant odor of alkalinizing agents in the colorant.

8 Claims, No Drawings

DYESTUFF FOR KERATIN FIBERS

BACKGROUND OF THE INVENTION

The invention has for an object alkali-containing colorants for keratin fibers, particularly human hair, that contain direct and/or oxidative dyes as well as encapsulated and unencapsulated perfume oils.

Coloring preparations are usually in the form of aqueous—preferably thickened—solutions or emulsions and besides dyes contain, for example, fatty alcohols and/or other oil components, emulsifiers and surfactants and optionally alcohols. As a rule, oxidation colorants consist of two components (i) the dye carrier composition containing the dye and (ii) the oxidant preparation, said components being mixed with each other shortly before use, and the mixture then being applied to the hair to be dyed. All oxidation colorants known from the prior art contain a certain amount of alkalinizing agent to enable and accelerate dye transport by interaction with hydrogen peroxide. Most of these oxidation colorants contain ammonia or monoethanolamine as the alkalinizing agent. Ammonia is known for its pungent odor, but because of its small molecular size exerts the most effective action in the formation of the coloring dye molecules in an oxidation colorant. Monoethanolamine is to a large extent odorless, but in an oxidation colorant generates a musty odor and because of its greater molecular size is less effective than ammonia.

WO 95/16432 describes a perfume system for use in hair-care and styling agents and wherein the encapsulated perfume and the unencapsulated perfume must have a different scent.

SUMMARY OF THE INVENTION

The purpose was therefore to develop an agent which even when alkalinizing agents with an intense odor are used would make it possible to eliminate or mask unpleasant odors in a satisfactory manner.

Surprisingly, we have now found that excellent covering of the unpleasant odor of alkalinizing agents can be achieved when to the colorant is added a perfume of the same scent type in encapsulated as well as in an unencapsulated form.

Hence, the present invention has for an object a colorant for keratin fibers containing direct and/or oxidative dyes, characterized in that it contains a perfume system consisting of an encapsulated (preferably microencapsulated) perfume and an unencapsulated perfume of the same perfume composition, wherein the ratio of encapsulated to unencapsulated perfume is from about 0.5:3 to 3:0.5 and preferably from 1:1 to 1:2 or 2:1.

The encapsulation of the perfume can be carried out by methods known from the literature, for example from WO 00/36931 A1. The encapsulation of the perfume is preferably carried out by use of modified starch and/or an oligosaccharide (particularly mannitol) as encapsulation material, the particle size of the encapsulated perfume being from 5 nm to 5 mm and preferably from 30 μm to 800 μm. The perfume content of the encapsulated material is preferably from 35 to 65 weight percent.

In the perfume system, it is possible to use all common and known perfume oils (particularly the perfumes known to be used in hair colorants)—alone or in combination with one another—provided they can be encapsulated.

The colorant of the invention preferably contains oxidation dye precursors which give rise to the color by the action of an oxidant, for example hydrogen peroxide, or in the presence of atmospheric oxygen.

Suitable oxidation dye precursors are, for example, the following developers and couplers as well as self-coupling compounds.

(i) Developers: 1,4-diaminobenzene (p-phenylenediamine), 1,4-diamino-2-methyl-benzene (p-toluylenediamine), 1,4-diamino-2,6-dimethylbenzene, 1,4-diamino-3,5-diethyl-benzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 2-[2-(acetylamino)ethoxy]-1,4-diaminobenzene, 4-phenylaminoaniline, 4-dimethylaminoaniline, 4-diethylaminoaniline, 4-dipropylaminoaniline, 4-[ethyl-(2-hydroxyethyl)amino]aniline, 4-[di(2-hydroxyethyl)amino]-aniline, 4-[di(2-hydroxyethyl)amino]-2-methylaniline, 4-[(2-methoxyethyl)amino]aniline, 4-[(3-hydroxypropyl)amino]aniline, 4-[(2,3-dihydroxypropyl)amino]aniline, 1,4-diamino-2-(2-hydroxyethyl)benzene, 1,4-di-amino-2-(1-methylethyl)benzene, 1,3-bis[(4-aminophenyl)-(2-hydroxyethyl)amino]-2-propanol, 1,4-bis[(4-aminophenyl)amino]butane, 1,8-bis(2,5-di-aminophenoxy)-3,6-dioxaoctane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)-amino]methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methyl.-phenyl)methyl]-1H-pyrazole, 1-[(4-chlorophenyl)methyl]4,5-diamino-1H-pyrazole, 4,5-diamino-1-methyl-1H-pyrazole, 2-aminophenol, 2-amino-6-methylphenol and 2-amino-5-methylphenol, alone or in admixture with one another.

(ii) Couplers: N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 5-amino-2-chloro-6-methylphenol, 3-aminophenol, 2-[(3-hydroxyphenyl)amino] acetamide, 5-[(2-hydroxyethyl)amino]4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxy-phenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione, alone or in admixture with one another.

(iii) Self-coupling compounds: 2-amino-5-methylphenol, 2-amino-6-methylphenol, 2-amino-5-ethoxyphenol or 2-propylamino-5-aminopyridine.

Among the aforesaid oxidation dyes, the following compounds, alone or in combination with one another, are particularly preferred: 2,5-diaminotoluene, 2,4-diaminophenoxy-ethanol, resorcinol, 2-methylresorcinol, m-aminophenol, 4-amino-m-cresol, 4-amino-2-hydroxytoluene, 6-amino-m-cresol, 2-amino-4-hydroxyethylaminoanisol, 1-naphthol, hydroxyethyl-3,4-methylenedioxyaniline, 2,5-diaminophenylethanol, N,N-bis(2-hydroxyethyl)-p-phenylenediamine, phenylmethylpyrazolone, 1-hydroxyethyl-4,5-diaminopyrazole and 2-amino-6-chloro-4-nitrophenol or the salts thereof.

The total amount of the oxidation dye precursors contained in the agent of the invention is about 0.01 to 12 weight percent and particularly about 0.2 to 6 weight percent.

Moreover, to achieve certain color shades, the colorant can contain common natural and/or synthetic direct dyes, for example vegetable dyes such as henna or indigo, triphenylmethane dyes, aromatic nitro dyes, azo dyes, quinone dyes, cationic or anionic dyes.

Suitable synthetic dyes are, for example: hydroxyethyl-2-nitro-p-toluidine, 2-hydroxyethylpicramic acid, 4-nitrophenylaminourea, tri(4-amino-3-methylphenyl)-carbenium chloride (Basic Violet 2), 1,4-diamino-9,10-anthracenedione (Disperse Violet 1), 1,4-bis[(2-hydroxyethyl)amino]-2-nitrobenzene, 1-(2-hydroxyethyl)amino-2-nitro-4-[di(2-hydroxyethyl)amino]benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1-[(2-hydroxyethyl)-amino]-2-nitrobenzene hydrochloride (HC Blue No. 12), 4-[di(2-hydroxyethyl)amino]-1-[(2-methoxyethyl)amino]-2-nitrobenzene (HC Blue No. 11), 1-[(2,3-dihydroxypropyl)-amino]4-[methyl-(2-hydroxyethyl)amino]-2-nitrobenzene (HC Blue No. 10), 1-[(2,3-dihydroxypropyl)amino]4-[ethyl-(2-hydroxyethyl)amino]-2-nitrobenzene hydrochloride (HC Blue No. 9), 1-(3-hydroxypropylamino) 4-[di(2-hydroxyethyl)amino]-2-nitrobenzene (HC Violet No. 2), 1-methylamino-4-[methyl-(2,3-dihydroxypropyl)amino]-2-nitrobenzene (HC Blue No. 6), 2-[(4-amino-2-nitrophenyl)amino]-5-dimethylaminobenzoic acid (HC Blue No. 13), 1-amino-4-[(2-hydroxyethyl)amino]-2-nitrobenzene (HC Red No. 7), 2-amino-4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red. No. 3), 4-amino-3-nitrophenol, 4-[(2-hydroxyethyl)amino]-3-nitrophenol, 1-[(2-aminoethyl)amino]4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di-(2,3-dihydroxypropyl)amino]-2-nitrobenzene (HC Red No. 11), 2-[(2-hydroxyethyl)amino]4,6-dinitrophenol, 4-ethylamino-3-nitrobenzoic acid, 2-[(4-amino-2-nitrophenyl)amino]benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzoxazine (HC Red No. 14), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]4-nitrobenzene, 4-[(2,3-dihydroxypropyl)amino]-3-nitro-1-trifluoro-methylbenzene (HC Yellow No. 6), 1-chloro-2,4-bis[(2-hydroxyethyl)amino]-5-nitro-benzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 1,4-di[(2,3-dihydroxypropyl)amino]-9,10-anthraquinone, 1-[(2-hydroxyethyl)amino]4-methyl-amino-9,10-anthraquinone (C.I. 61505, Disperse Blue No. 3), 2-[(2-aminoethyl)amino]-9,10-anthraquinone (HC Orange No. 5), 1-hydroxy-4-[(4-methyl-2-sulfophenyl)amino]-9, 10-anthraquinone, 1-[(3-aminopropyl)amino]4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (C.I. 62015, Disperse Red No. 11, Solvent Violet No. 26), 1,4-dihydroxy-5,8-bis[(2-hydroxyethyl)amino]-9,10-anthraquinone (C.I. 62500, Disperse Blue No. 7, Solvent Blue No. 69), 9-(dimethylamino)benzo[a]-phenoxazin-7-ium chloride (C.I. 51175; Basic Blue No. 6), di[4-(diethylamino)phenyl][4-(ethylamino)naphthyl]carbenium chloride (C.I. 42595; Basic Blue No. 7), 3,7-di(dimethylamino)phenothiazin-5-ium chloride (C.I. 52015; Basic Blue No. 9), di[4-(dimethylamino)phenyl][4-(phenylamino)naphthyl]carbenium chloride (C.I. 44045; Basic Blue No. 26), 2-[(4-(ethyl-(2-hydroxyethyl)amino)phenyl)azo]-6-methoxy-3-methylbenzothiazolium methylsulfate (C.I. 11154; Basic Blue No. 41), 8-amino-2-bromo-5-hydroxy-4-imino-6-{[(3-trimethylammonio)phenyl]amino}-1(4H)-naphthalenone chloride (C.I. 56059; Basic Blue No. 99), bis[4-(dimethylamino)phenyl][4-(methylamino)phenyl]carbenium chloride (C.I. 42535; Basic Violet No. 1), tris[4-(dimethylamino)phenyl]carbenium chloride (C.I. 42555; Basic Violet No. 3), 2-[3,6-(diethylamino)dibenzopyranium-9-yl]benzoyl chloride (C.I. 45170; Basic Violet No. 10), di(4-aminophenyl)-(4-amino-3-methylphenyl)carbenium chloride (C.I. 42510; Basic Violet No. 14), 1,3-bis[(2,4-diamino-5-methylphenyl)azo]-3-methylbenzene (C.I. 21010; Basic Brown No. 4), 1-[(4-aminophenyl)azo]-7-(trimethylammonio)-2-naphthol chloride (C.I. 12250; Basic Brown No. 16), 1-[(4-amino-2-nitrophenyl)azo]-7-(trimethylammonio)-2-naphthol chloride, 1-[(4-amino-3-nitrophenyl)azo]-7-(trimethylammonio)-2-naphthol chloride (C. I. 12251; Basic Brown No. 17), 3,7-diamino-2,8-dimethyl-5-phenylphenazinium chloride (C. 50240; Basic Red. No. 2), 1,4-dimethyl-5-{[4-(dimethylamino)phenyl]azo}-1,2,4-triazolium chloride (C.I. 11055; Basic Red No. 22), 2-hydroxy-1-[(2-methoxyphenyl)azo]-7-(trimethylammonio)-naphthalene chloride (C.I. 12245; Basic Red No. 76), 2-{2-[(2,4-dimethoxyphenyl)-amino]ethenyl}-1,3,3-trimethyl-3H-indol-1-ium chloride (C.I. 48055; Basic Yellow No. 11), 3-methyl-1-phenyl-4-{[3-(trimethylammonio)phenyl]azo}pyrazol-5-one chloride (C.I. 12719; Basic Yellow No. 57), bis[4-(diethylamino)phenyl]phenylcarbenium hydrogen sulfate (1:1) (C.I. 42040; Basic Green No. 1), 1-[di-(2-hydroxyethyl)amino]-3-methyl-4-[(4-nitrophenyl)azo]benzene (C.I. 11210, Disperse Red No. 17), 4-[(4-aminophenyl)azo]-1-[di-(2-hydroxyethyl)amino]-3-methylbenzene (HC Yellow No. 7), 2,6-diamino-3-[(pyridin-3-yl)-azo]pyridine, disodium 6-hydroxy-5-[(4-sulfophenyl)azo]-2-naphthalenesulfonate (C.I. 15985; Food Yellow No. 3; FD&C Yellow No. 6), disodium 2,4-dinitro-1-naphthol-7-sulfonate (C.I. 10316; Acid Yellow No. 1; Food Yellow No. 1), 2-(indan-1,3-dion-2-yl)-quinolin-x,x-sulfonic acid (mixture of mono- and disulfonic acid) (C.I. 47005; D&C Yellow No. 10; Food Yellow No. 13; Acid Yellow No. 3), trisodium 5-hydroxy-1-(4-sulfophenyl)-4-[(4-sulfophenyl)azo]pyrazole-3-carboxylate (C.I. 19140; Food Yellow No. 4; Acid Yellow No. 23), 9-(2-carboxyphenyl)-6-hydroxy-3H-xanthen-3-one (C.I. 45350; Acid Yellow No. 73; D&C Yellow No. 8), sodium 5-[(2,4-dinitrophenyl)amino]-2-phenylaminobenzene-sulfonate (C.I. 10385; Acid Orange No. 3), monosodium 4-[(2,4-dihydroxyphenyl)-azo]benzenesulfonate (C.I. 14270; Acid Orange No. 6), sodium 4[(2-hydroxynaphth-1-yl)azo]benzenesulfonate (C.I. 15510; Acid Orange No. 7), sodium 4-[(2,4-dihydroxy-3-[(2,4-dimethylphenyl)azo]phenyl)azo]benzenesulfonate (C.I. 20170; Acid Orange No. 24), disodium 4-hydroxy-3-[(4-sulfonaphth-1-yl)azo]-1-naphthalenesulfonate (C.I. 14720; Acid Red No. 14), trisodium 6-hydroxy-5-[(4-sulfonaphth-1-yl)azo]-2,4-naphthalenedisulfonate (C.I. 16255; Ponceau 4R; Acid Red No. 18), trisodium 3-hydroxy-4-[(4-sulfonaphth-1-yl)azo]-2,7-naphthalenedisulfonate (C.I. 16185; Acid Red No. 27), disodium 8-amino-1-hydroxy-2-(phenylazo)-3,6-naphthalenedisulfonate (C.I. 17200; Acid Red No. 33), disodium 5-(acetylamino)4-hydroxy-3-[(2-methylphenyl)azo]-2,7-naphthalenedisulfonate (C.I. 18065; Acid Red No. 35), disodium 2-(3-hydroxy-2,4,5,7-tetraiododibenzopyran-6-on-9-yl)benzoate (C.I. 45430; Acid Red No. 51), N-[6-(diethylamino)-9-(2,4-disulfophenyl)-3H-xanthen-3-ylidene]-N-ethylethaneammonium hydroxide inner salt, sodium salt (C.I. 45100; Acid Red No. 52), disodium 8-{[4-(phenylazo)phenyl]azo}-7-naphthol-1,3-disulfonate (C.I. 27290; Acid Red No. 73); 2',4',5',7'-tetrabromo-3',6'-dihydroxyspiro{isobenzofuran-1(3H), 9'-[9H]xanthen}-3-one disodium salt (C.I. 45380; Acid Red No. 87), 2',4',5',7'-tetrabromo-4,5,6,7-tetrachloro-3',6'- dihydroxyspiro{isobenzofuran-1-3H), 9'[9H]-xanthen}-3-one disodium salt (C.I. 45410; Acid Red No. 92), 3',6'-dihydroxy-4',5'-diiodospiro{isobenzofuran-1(3H), 9(9H)-xanthen}-3-one disodium salt (C.I. 45425; Acid Red No. 95), (2-sulfophenyl)di[4-(ethyl((4-sulfophenyl)methyl)amino)phenyl]carbenium disodium salt, betaine (C.I. 42090; Acid Blue No. 9; FD&C Blue No. 1), 1,4-bis[(2-sulfo-4-methylphenyl)amino]-9,10-anthraquinone disodium salt (C.I. 61 570; Acid Green No. 25), bis[4-(dimethylamino)phenyl]-(3,7-disulfo-2-hydroxynaphth-1-yl)carbenium inner salt, monosodium salt (C.I. 44090; Food Green No. 4; Acid Green No. 50), bis[4-(diethylamino)phenyl](2,4-disulfophenyl)carbenium inner salt, sodium salt (2:1) (C.I. 42045; Food Blue No. 3; Acid Blue No. 1), bis[4-[diethylamino)phenyl](5-hydroxy-2,4-disulfophenyl)carbenium inner salt, calcium salt (2:1) (C.I. 42051; Acid Blue No. 3), sodium 1-amino-4-(cyclohexylamino)-9,10-anthraquinone-2-sulfonate (C.I. 62 045; Acid Blue No. 62), disodium 2-(1,3-dihydro-3-keto-5-sulfo-2H-indol-2-ylidene)-2,3-dihydro-3-keto-1H-indol-5-sulfonate (C.I. 73015; Acid Blue No. 74), 9-(2-carboxyphenyl)-3-[(2-methylphenyl)amino]-6-[(2-methyl-4-sulfophenyl)amino]xanthylium inner salt, monosodium salt (C.I. 45190; Acid Violet No. 9), 1-hydroxy-4-[(4-methyl-2-sulfophenyl)amino]-9,10-anthraquinone sodium salt (C.I. 60730; D&C Violet No. 2; Acid Violet No. 43), bis{3-nitro-4-[(4-phenylamino)-3-sulfophenylamino]phenyl} sulfone (C.I. 10410; Acid Brown No. 13), disodium 5-amino-4-hydroxy-6-[(4-nitrophenyl)azo]-3-(phenylazo)-2,7-naphthalenedisulfonate (C. I. 20470; Acid Black No. 1), 3-hydroxy-4-[(2-hydroxynaphth-1-yl)azo]-7-nitro-1-naphthalenesulfonic acid chromium complex (3:2) (C.I. 15711); Acid Black No. 52), disodium 3-[(2,4-dimethyl-5-sulfophenyl)azo]4-hydroxy-1-naphthalenesulfonate (C.I. 14700; Food Red No. 1; FD&C Red No. 4), tetrasodium 4-(acetylamino)-5-hydroxy-6-[(7-sulfo-4-[(4-sulfophenyl)azo]naphth-1-yl)azo]-1,7-naphthalenedisulfonate (C.I. 28 440; Food Black No. 1) and sodium 3-hydroxy-4-(3-methyl-5-keto-1-phenyl-4,5-dihydro-1H-pyrazol-4-yl-azo)naphthalene-1-sulfonate, chromium complex (Acid Red No. 195), 3',3",4,5,5',5",6,7-octabromophenolsulfonphthalein (Tetrabromophenol Blue), 1-((4-amino-3,5-dimethylphenyl)-(2,6-dichlorophenyl)methylene)-3,5-dimethyl-4-imino-2,5-cyclohexadiene combined with phosphoric acid (1:1) (Basic Blue 77), 2',4',5',7'-tetrabromo-4,5,6,7-tetrachloro-3',6'-dihydroxyspiro{isobenzofuran-1-(3H), 9'[9H]xanthen}3-one disodium salt (Acid Red No. 92), N,N-di(2-hydroxy-ethyl)-3-methyl-4-[(4-nitrophenyl)azo]aniline (Disperse Red 17), disodium 2,4-dinitro-1-naphthol-7-sulfonate (Acid Yellow 1), sodium 4-[(2-hydroxynaphthalen-1-yl)azo]benzenesulfonate (Acid Orange 7), 2-((4-(ethyl-(2-hydroxyethyl)amino)-2-methylphenyl)azo)-5-nitro-1,3-thiazole (Disperse Blue 106), 2,4-dinitro-1-naphthol, 2-[(4-aminophenyl)azo]-1,3-dimethyl-1H-imidazol-3-ium chloride, 1-methyl-4-(methylphenylhydrazono)methyl)pyridinium methosulfate, 2-{[4-(dimethylamino)phenyl]azo}-1,3-dimethyl-imidazolium chloride, 2-((4-((4-methoxyphenyl)amino)phenyl)azo)-1,3-dimethyl-1H-imidazol-3-ium chloride and 1,3-dimethyl-2-((4-((phenylmethyl)amino)phenyl)azo)-1H-imidazol-3-ium chloride, alone or in combination with one another.

Particularly preferred among the aforesaid direct dyes are the following compounds, alone or in combination with one another: hydroxyethyl-2-nitro-p-toluidine, 2-hydroxyethylpicramic acid, 4-nitrophenylaminourea, tri(4-amino-3-methylphenyl)carbenium chloride (Basic Violet 2), 1,4-diamino-9,10-anthracenedione (Disperse Violet 1), 1-(2-hydroxyethyl)amino-2-nitro-4-[di(2-hydroxyethyl)amino]

benzene (HC Blue No. 2), 4-[ethyl-(2-hydroxyethyl)amino]-1-[(2-hydroxyethyl)amino]-2-nitrobenzene hydrochloride (HC Blue No. 12), 1-amino-4-[di(2-hydroxyethyl)amino]-2-nitrobenzene hydrochloride (HC Red No. 13), 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-chloro-6-ethylamino-4-nitrophenol, 2-amino-6-chloro-4-nitrophenol, 4-[(2-hydroxyethyl)amino]-3-nitro-1-trifluoromethylbenzene (HC Yellow No. 13), 8-amino-2-bromo-5-hydroxy-4-imino-6-{[3-(trimethylammonio)phenyl]amino}-1(4H)-naphthalenone chloride (C.I. 56059; Basic Blue No. 99), 1-[(4-aminophenyl)azo]-7-(trimethylammonio)-2-naphthol chloride (C.I. 12250; Basic Brown No. 16), 1-[(4-amino-2-nitrophenyl)azo]-7-(trimethylammonio)-2-naphthol chloride (Basic Brown No. 17), 2-hydroxy-1-[(2-methoxyphenyl)azo]-7-(trimethylammonio) naphthalene chloride (C.I. 12245; Basic Red No. 76), 3-methyl-1-phenyl-4-{[3-(trimethylammonio)phenyl]azo}pyrazol-5-one chloride (C.I. 12719; Basic Yellow No. 57) and 2,6-diamino-3-[(pyridin-3-yl)azo]pyridine as well as the salts thereof.

The total amount of direct dyes in the colorant of the invention is about 0.01 to 7 weight percent and preferably about 0.2 to 4 weight percent.

Other known and common dyes used for hair-dyeing that can be contained in the colorant of the invention are described in, among other publications, E. Sagarin "Cosmetics, Science and Technology", Interscience Publishers Inc., New York (1957), pages 503 ff, H. Janistyn, "Handbuch der Kosmetika und Riechstoffe" [Manual of Cosmetics and Fragrances], vol. 3 (1973), pages 388 ff and K. Schrader "Grundlagen und Rezepturen der Kosmetika" [Fundamentals and Formulations of Cosmetics], 2nd edition (1989), pages 782-815, the disclosures of which are hereby included by reference.

Although oxidation dyes are preferred, it is, of course, also possible for the colorant of the invention to be in the form of a nonoxidative colorant based on the aforesaid direct dyes.

Moreover, the colorant of the invention can contain antioxidants, for example ascorbic acid, thioglycolic acid or sodium sulfite, as well as complexing agents for heavy metals, for example an ethylenediaminetetraacetate or nitriloacetic acid, in an amount of up to about 0.5 weight percent. Naturally, the afore-described hair colorant can optionally contain other additives commonly used in hair colorants, for example higher fatty alcohols, thickeners, for example homopolymers of acrylic acid, vegetable gums, cellulose derivatives and starch derivatives, algal polysaccharides, amphiphilic associative thickeners, furthermore preservatives; complexing agents; solvents such as water, the lower aliphatic alcohols, for example aliphatic alcohols with 1 to 4 carbon atoms, such as ethanol, propanol and isopropanol, or glycols, such as glycerol and 1,2-propylene glycol; wetting agents or emulsifiers from the classes of anionic, cationic, amphoteric or nonionic surface-active substances; further-more softeners; vaselines, silicone oils, paraffin oil, polysorbates and fatty acids as well as hair-care agents, such as cationic polymers or resins, lanolin derivatives, cholesterol, vitamins, pantothenic acid and betaine. The said constituents are employed in amounts normally used for such purposes, for example the wetting agents and emulsifiers at a concentration from 0.1 to 30 weight percent and the hair-care agents at a concentration from 0.1 to 5.0 weight percent.

For nonoxidative colorants based on direct dyes, the pH of the colorant of the invention is in the range from about 5 to 10, preferably from 6 to 9, whereas for oxidative colorants based on oxidation dye precursors the pH is in the range from about 6 to 12 and preferably from 9 to 11, the pH of the ready-to-use oxidation hair colorant (namely of the mixture of the hair colorant of the invention and the oxidant) is about 5.5 to 10 and preferably 6 to 9.

Depending on the composition and the desired pH of the colorant, the pH is adjusted preferably with ammonia or an organic amine such as a glucamine, aminomethyl-propanol, monoethanolamine or triethanolamine, with an inorganic base, for example sodium hydroxide, potassium hydroxide, sodium carbonate or calcium hydroxide, or with an organic or inorganic acid, for example lactic acid, citric acid, acetic acid or phosphoric acid.

The colorant of the invention is preferably packaged in the form of an aqueous or aqueous-alcoholic preparation, for example as a thickened solution, as an emulsion or as a cream or gel.

To be used for oxidative dyeing, as a rule, the afore-described colorant is mixed with an oxidant just before use, and a sufficient amount of the ready-to-use mixture, as a rule about 60 to 200 grams, is applied to the fibers.

If the colorant of the invention contains no oxidation dye precursors or contains oxidation dye precursors that are readily oxidized by atmospheric oxygen, the colorant can be applied to keratin fibers without prior mixing with an oxidant.

Suitable oxidants for the development of the coloration are mainly hydrogen peroxide and the compounds of addition thereof to urea, melamine or sodium borate, in the form of a 1 to 12% and preferably 1.5 to 6% aqueous solution. The mixing ratio of colorant to oxidant depends on the concentration of the oxidant and as a rule is about 5:1 to 1:2 and preferably 1:1, the oxidant content of the ready-to-use preparation preferably being from about 0.5 to 8 weight percent, and particularly from 1 to 4 weight percent.

The ready-to-use colorant is allowed to act on the keratin fibers (for example human hair) at 15 to 50° C. for about 10 to 45 minutes and preferably for about 15 to 30 minutes, after which the fibers are rinsed with water and dried. Optionally, this rinsing is followed by washing with a shampoo and then, optionally, post-rinsing with a weak organic acid, for example tartaric acid. The keratin fibers are then dried.

The combination according to the invention of encapsulated (preferably microencapsulated) perfume and unencapsulated perfume of the same composition can be contained either in the dye carrier composition or in the oxidant preparation.

Another object of the present invention is the use for removing or masking the unpleasant odors of alkalinizing agents, particularly in hair colorants, of a perfume system consisting of an encapsulated (preferably microencapsulated) perfume and an unencapsulated perfume of the same composition, wherein the ratio of encapsulated perfume to unencapsulated perfume is about 0.5:3 to 3:0.5 and preferably 1:1 to 1:2 or 2:1, The combination according to the invention of encapsulated (preferably microencapsulated) perfume and unencapsulated perfume of the same composition permits outstanding covering of the unpleasant odor of alkalinizing agents (for example ammonia or organic amines), particularly in colorants for keratin fibers.

The following examples will explain the subject matter of the invention in greater detail without limiting its scope.

EXAMPLES

Example 1

Anionic Oxidation Hair Colorant in Cream Form 6.0000 g of stearyl alcohol
5.0000 g of cetyl alcohol
8.0000 g of Cocamide MEA (Oramide® ML 115, supplied by Seppic)
4.0000 g of fatty alcohol alkoxylate (Volpo® S20, supplied by Seppic)
5.0000 g of sodium lauryl ether sulfate
1.3620 g of 4-aminophenol
0.5000 g of 1-naphthol
0.0136 g of resorcinol
0.0034 g of 2-amino-6-chloro-4-nitrophenol
12.0000 g of ammonia, 25% aqueous solution
1.0000 g of disodium ethylenediaminetetraacetate
1.0000 g of ascorbic acid
0.2500 g of perfume oil (CURLY D 40 092 E PM unencapsulated, supplied by Symrise)
0.2500 g of perfume oil (CURLY D 40 092 E PM encapsulated, supplied by Symrise)
to 100.0000 g water Just before use, 50 g of the above hair colorant was mixed with 50 g of a 6% aqueous hydrogen peroxide solution. This gave a homogeneous, cosmetically appealing colorant preparation. The resulting mixture was then applied to naturally blond hair. After an exposure time of 30 minutes at 40° C., the hair was rinsed with water and dried. The hair had a lustrous, copper-red color. During the mixing and exposure time, the colorant of the invention gave off only a slight odor of ammonia.

Example 2

Cationic Oxidation Hair Colorant for Bright Coloring in Cream Form

Component (A): Creamy Dye Carrier Composition
  6.00 g of cetylstearyl alcohol
  8.00 g of stearyl alcohol
  8.00 g of Cocamide MEA (Comperlan® 100, supplied by Cognis)
  6.00 g of fatty alcohol ethoxylate (Brij® 76, supplied by ICI)
  1.00 g of oleic acid
  4.00 g of behentrimonium chloride (Genamin® KDMP, supplied by Croda)
  0.50 g of para-phenylenediamine
  0.07 g of resorcinol
  1.00 g of disodium ethylenediaminetetraacetate
  0.30 g of sodium sulfite
  12.00 g of ammonia, 25% aqueous solution
  8.00 g of ethanol
  0.40 g of perfume oil (466 322 LUCRECE L 20 023 K encapsulated, supplied by Symrise)
  0.30 g of perfume oil (466 322 LUCRECE L 20 023 K unencapsulated, supplied by Symrise)
  to 100.00 g water Component B: Hydrogen Peroxide Emulsion
  10.00 g of cetylstearyl alcohol
  1.50 g of cholesterol
  4.00 g of sodium lauryl alcohol diethylene glycol ether sulfate, 28% aqueous solution
  35.00 g of hydrogen peroxide, 35% aqueous solution
  to 100.00 g water Before use, 40 g of the liquid dye carrier composition (A) was mixed with 80 g of the hydrogen peroxide emulsion (B) in an (A):(B) mixing ratio of 1:2, and 120 g of this mixture was applied to gray human hair. After an exposure time of 20 minutes at room temperature, the hair was rinsed with water and dried. The hair thus treated had a uniform bright-brown color from the hair roots to the hair tips. The ammonia odor given off by the colorant both during the mixing and during the exposure time was only slight.

Example 3

Cationic Oxidation Hair Colorant in Cream Form 4.00 g of cetylstearyl alcohol
5.00 g of behenyl alcohol
12.00 g of Cocamide MEA (Rewomid C212, supplied by Goldschmidt)
2.00 g of ethylene glycol distearate
5.00 g of distearyldimethylammonium chloride (Arquad® 2HAT-75, supplied by Akzo Nobel)
8.00 g of monoethanolamine
1.30 g of 1-methyl-2,5-diaminobenzene
1.00 g of beeswax
0.65 g of resorcinol
0.50 g of keratin hydrolyzate
0.50 g of silk protein hydrolyzate
0.52 g of 2-amino-6-chloro-4-nitrophenol
1.00 g of disodium ethylenediaminetetraacetate
0.30 g of ascorbic acid
0.40 g of perfume oil (AFFINITY L 20 017 P encapsulated, supplied by Symrise)
0.20 g of perfume oil (AFFINITY L 20 017 P unencapsulated, supplied by Symrise)
to 100.00 g water Just before use, 50 g of the above hair colorant was mixed with 50 g of a 12% aqueous hydrogen peroxide solution. The resulting mixture was then applied to naturally blond hair. After an exposure time of 30 minutes at 40° C., the hair was rinsed with water and dried. The hair had a uniform, strong brown color shade. During the mixing and exposure time, the colorant of the invention gave off an only slight amine odor.

Example 4

Cationic Oxidation Hair Colorant

Component A:
  6.0000 g of stearyl alcohol
  5.0000 g of behenyl alcohol
  8.0000 g of Cocamide MEA
  2.0000 g of Steareth-20
  2.0000 g of distearyldimethylammonium chloride
  2.0000 g of isopropyl alcohol
  1.3620 g of 4-aminophenol 0.5000 g of 1-naphthol
0.0136 g of resorcinol
0.0034 g of 2-amino-6-chloro-4-nitrophenol
12.0000 g of ammonia, 25% aqueous solution
0.1600 g of (4-{ethyl-[(2-hydroxyethyl)amino]-2-nitrophenyl}amino)-ethanol hydrochloride (HC BLUE NO. 12)
0.1700 g of 3-{[2-nitro-4-(trifluoromethyl)phenyl]amino}-1,2-propanediol (HC YELLOW NO. 6)
0.0120 g of 1-N-hydroxyethylamino-2-nitro-4-methylbenzene
0.0350 g of 3-(4-amino-2-chloro-5-nitrophenyl)amino-1,2-propanediol
to 100.0000 g water Component B: Hydrogen Peroxide Emulsion 10.00 g of cetylstearyl alcohol
1.50 g of cholesterol
4.00 g of sodium lauryl alcohol diethylene glycol ether sulfate, 28% aqueous solution
35.00 g of hydrogen peroxide, 35% aqueous solution
0.30 g of perfume oil (AFFINITY L 20 017 P unencapsulated, supplied by Symrise)
0.50 g of perfume oil (AFFINITY L 20 017 P encapsulated, supplied by Symrise)
to 100.00 g water Before use, components A and B were mixed with each other 1:1, and the resulting creamy colorant composition was then applied to washed and towel-dried natural blond hair. After an exposure time of about 20 to 25 minutes, the hair was rinsed with water, washed with a shampoo and then again rinsed with water. This produced a lustrous, intense red shade. The ready-to-use colorant gave off only a slight amine odor.

Example 5

Anionic Oxidation Hair Colorant 8.00 g of cetylstearyl alcohol
1.00 g of stearyl alcohol
8.00 g of Cocamide DEA
2.00 g of Oleth-30
2.50 g of sodium lauryl ether sulfate
7.00 g of ethanol, aqueous
0.10 g of 2,5-diaminotoluene sulfate
1.65 g of 4-amino-3-methylphenol
0.70 g of resorcinol
0.70 g of alpha-naphthol
0.30 g of 5-amino-2-methylphenol
0.20 g of 2-amino-6-chloro-4-nitrophenol
0.15 g of perfume oil (CURLY D 40 092 E PM encapsulated, supplied by Symrise)
0.25 g of perfume oil (CURLY D 40 092 E PM unencapsulated, supplied by Symrise)
to 100.00 g water Just before use, 50 g of the above hair colorant was mixed with 50 g of a 6% aqueous hydrogen peroxide solution. This gave a homogeneous, cosmetically appealing colorant preparation. The resulting mixture was then applied to naturally blond hair. After an exposure time of 30 minutes at 40° C., the hair was rinsed with water and dried. The hair had a trendy red color. During the mixing and exposure time, the colorant of the invention gave off only a slight odor of ammonia.

Unless otherwise indicated, all percentages given in the present patent application are by weight.

The invention claimed is:

1. Colorant for keratin fibers, said colorant containing
   at least one dye selected from the group consisting of direct dyes and oxidative dyes; and
   a perfume system consisting of an encapsulated perfume and an unencapsulated perfume;
   wherein a ratio of the encapsulated perfume to the unencapsulated perfume is from 0.5:3 to 3:0.5 and the encapsulated perfume consists of an encapsulation material and the unencapsulated perfume.

2. Colorant as defined in claim 1, wherein the ratio of the encapsulated perfume to the unencapsulated perfume is from 1:2 to 1:1 or from 1:1 to 2:1.

3. Colorant as defined in claim 1, containing at least one of the oxidative dyes in a total amount from 0.01 to 12 weight percent.

4. Colorant as defined in claim 1, containing at least one of the direct dyes in a total amount from 0.01 to 7 weight percent.

5. Colorant as defined in claim 1, consisting of a hair colorant.

6. A method of removing or masking an unpleasant odor of an alkalinizing agent in a colorant composition for keratin fibers, said colorant composition containing the alkalinizing agent and at least one dye, said at least one dye being selected from the group consisting of direct dyes and oxidative dyes, said method comprising including a perfume system in the colorant composition containing the alkalinizing agent and the at least one dye;
   wherein said perfume system consists of an encapsulated perfume and an unencapsulated perfume; and
   wherein a ratio of the encapsulated perfume to the unencapsulated perfume is from 0.5:3 to 3:0.5 and the encapsulated perfume consists of an encapsulation material and the unencapsulated perfume.

7. The method as defined in claim 6, wherein the ratio of the encapsulated perfume to the unencapsulated perfume is from 1:2 to 1:1 or from 1:1 to 2:1.

8. The method as defined in claim 6, wherein the alkalinizing agent is ammonia.

* * * * *